United States Patent
Shalon et al.

[11] Patent Number: 6,110,426
[45] Date of Patent: *Aug. 29, 2000

[54] METHODS FOR FABRICATING MICROARRAYS OF BIOLOGICAL SAMPLES

[75] Inventors: Tidhar Dari Shalon, Atherton; Patrick O. Brown, Stanford, both of Calif.

[73] Assignee: The Board of Trustees of the Leland Stanford Junior University, Stanford, Calif.

[*] Notice: This patent is subject to a terminal disclaimer.

[21] Appl. No.: 09/001,027

[22] Filed: Dec. 30, 1997

Related U.S. Application Data

[63] Continuation of application No. 08/477,809, Jun. 7, 1995, Pat. No. 5,807,522, which is a continuation-in-part of application No. 08/261,388, Jun. 17, 1994, abandoned.

[51] Int. Cl.[7] .................................................. G01N 15/06
[52] U.S. Cl. ............................. 422/68.1; 422/50; 435/6; 435/183.1; 436/51; 536/25.3
[58] Field of Search ..................... 422/50, 68.1; 435/6, 435/183.1; 436/501; 935/77, 78; 536/25.3

[56] References Cited

U.S. PATENT DOCUMENTS

| | | | |
|---|---|---|---|
| 3,730,844 | 5/1973 | Gilham et al. | 195/103.5 R |
| 4,071,315 | 1/1978 | Chateau | 23/230 B |
| 4,486,539 | 12/1984 | Ranki et al. | 436/504 |
| 4,556,643 | 12/1985 | Paau et al. | 436/501 |
| 4,563,419 | 1/1986 | Ranki et al. | 435/6 |
| 4,591,570 | 5/1986 | Chang | 436/518 |
| 4,670,380 | 6/1987 | Dattagupta | 435/6 |
| 4,677,054 | 6/1987 | White et al. | 435/6 |
| 4,683,195 | 7/1987 | Mullis et al. | 435/6 |

(List continued on next page.)

FOREIGN PATENT DOCUMENTS

| | | |
|---|---|---|
| 0717113 | 6/1996 | European Pat. Off. . |
| 721016A2 | 7/1996 | European Pat. Off. . |
| 2248840 | 1/1993 | United Kingdom . |
| WO 89/10977 | 5/1989 | WIPO . |
| WO 90/03382 | 4/1990 | WIPO . |
| WO 92/10588 | 6/1992 | WIPO . |
| WO 93/09668 | 5/1993 | WIPO . |
| WO 92/22680 | 11/1993 | WIPO . |
| WO 95/00530 | 1/1995 | WIPO . |
| WO 95/11995 | 5/1995 | WIPO . |
| WO 95/15970 | 6/1995 | WIPO . |
| WO 95/21944 | 8/1995 | WIPO . |
| WO 95/25116 | 9/1995 | WIPO . |
| WO 96/17958 | 6/1996 | WIPO . |
| WO 97/10365 | 3/1997 | WIPO . |

OTHER PUBLICATIONS

McGall, et al., "The Efficiency of Light–Directed Synthesis of DNA Arrays on Glass Substrates", *J. Am. Chem. Soc.*, 119:5081–5090 (1997).

Pirrung, et al., "Comparison of Methods for Photochemical Phosphoramidite–Based DNA Synthesis", *J. Org. Chem.*, 60:6270–6276(1995).

Billings et al., "New Techniques for Physical Mapping of the Human Genome," *FASEB*, 5:28–34 (1991).

Chee, et al., "Accessing Genetic Information with High–Density DNA Arrays", *Science*, 274:610–614 (1996).

Drmanac et al., "DNA Sequence Determination by Hybridization: A Strategy for Efficient Large–Scale Sequencing," *Science*, 260:1649–1652 (1993).

(List continued on next page.)

*Primary Examiner*—Ardin H. Marschel
*Attorney, Agent, or Firm*—Arnold White & Durkee

[57] ABSTRACT

A method and apparatus for forming microarrays of biological samples on a support are disclosed. The method involves dispensing a known volume of a reagent at each selected array position, by tapping a capillary dispenser on the support under conditions effective to draw a defined volume of liquid onto the support. The apparatus is designed to produce a microarray of such regions in an automated fashion.

4 Claims, 6 Drawing Sheets

(2 of 6 Drawing Sheet(s) Filed in Color)

U.S. PATENT DOCUMENTS

| | | | |
|---|---|---|---|
| 4,683,202 | 7/1987 | Mullis | 435/91 |
| 4,716,106 | 12/1987 | Chiswell | 435/6 |
| 4,731,325 | 3/1988 | Palva et al. | 435/6 |
| 4,755,458 | 7/1988 | Rabbani et al. | 435/5 |
| 4,767,700 | 8/1988 | Wallace | 435/6 |
| 4,868,104 | 9/1989 | Kurn et al. | 435/6 |
| 4,868,105 | 9/1989 | Urdea et al. | 435/6 |
| 4,921,805 | 5/1990 | Gebeyehu et al. | 435/270 |
| 4,981,783 | 1/1991 | Augenlicht | 435/6 |
| 5,013,669 | 5/1991 | Peters, Jr. et al. | 436/518 |
| 5,028,545 | 7/1991 | Soini | 436/501 |
| 5,064,754 | 11/1991 | Mills | 435/6 |
| 5,091,652 | 2/1992 | Mathies et al. | 250/458.1 |
| 5,100,777 | 3/1992 | Chang | 435/7.24 |
| 5,143,854 | 9/1992 | Pirrung et al. | 436/518 |
| 5,185,243 | 2/1993 | Ullmann et al. | 435/6 |
| 5,188,963 | 2/1993 | Stapleton | 435/299 |
| 5,200,051 | 4/1993 | Cozzette et al. | 204/403 |
| 5,200,312 | 4/1993 | Oprandy | 435/5 |
| 5,202,231 | 4/1993 | Drmanac et al. | 435/6 |
| 5,204,268 | 4/1993 | Matsumoto | 436/44 |
| 5,242,974 | 9/1993 | Holmes | 525/54.11 |
| 5,252,296 | 10/1993 | Zuckerman et al. | 422/116 |
| 5,252,743 | 10/1993 | Barrett et al. | 548/303.7 |
| 5,328,824 | 7/1994 | Ward et al. | 435/6 |
| 5,338,688 | 8/1994 | Deeg et al. | 436/180 |
| 5,348,855 | 9/1994 | Dattagupta et al. | 435/6 |
| 5,389,512 | 2/1995 | Sninsky et al. | 435/5 |
| 5,412,087 | 5/1995 | McGall et al. | 536/24.3 |
| 5,434,049 | 7/1995 | Okano et al. | 435/6 |
| 5,445,934 | 8/1995 | Fodor et al. | 435/6 |
| 5,472,842 | 12/1995 | Stokke et al. | 435/6 |
| 5,474,796 | 12/1995 | Brennan | 427/2.13 |
| 5,474,895 | 12/1995 | Ishii et al. | 435/6 |
| 5,510,270 | 4/1996 | Fodor et al. | 436/518 |
| 5,512,430 | 4/1996 | Gong | 435/5 |
| 5,514,543 | 5/1996 | Grossman | 435/6 |
| 5,514,785 | 5/1996 | Van Ness et al. | 536/22.1 |
| 5,516,641 | 5/1996 | Ullman et al. | 435/6 |
| 5,518,883 | 5/1996 | Soini | 435/6 |
| 5,545,531 | 8/1996 | Rava et al. | 435/6 |
| 5,556,748 | 9/1996 | Douglas | 435/6 |
| 5,556,752 | 9/1996 | Lockhart et al. | 435/6 |
| 5,563,060 | 10/1996 | Hozier | 435/240.23 |
| 5,578,832 | 11/1996 | Trulson et al. | 250/458.1 |
| 5,605,662 | 2/1997 | Heller et al. | 422/68.1 |
| 5,665,549 | 9/1997 | Pinkel et al. | 435/6 |
| 5,677,195 | 10/1997 | Winkler et al. | 436/518 |
| 5,744,305 | 4/1998 | Fodor | 435/6 |
| 5,795,716 | 8/1998 | Chee et al. | 435/6 |
| 5,800,992 | 9/1998 | Fodor et al. | 435/6 |
| 5,807,522 | 9/1998 | Brown et al. | 422/50 |

OTHER PUBLICATIONS

Drmanac et al., "Laboratory Methods: Reliable Hybridization of Oligonucleotides as Short as Six Nucleotides," *DNA and Cell Biology,* 9:527–534 (1990).

Drmanac et al., "Sequencing by Hybridization: Towards an Automated Sequencing of One Million M13 Clones Arrayed on Membranes," *Electrophoresis,* 13:566–573 (1992).

Ekins, et al., "Multianalyte Immunoassay: The Immunological 'Compact Disk' of the Future", *J. Clinical Immunoassay,* 13(4):169–181 (1990).

Fodor et al., "Light–Directed, Spatially Addressable Parallel Chemical Synthesis," *Science,* 251:767–773 (1991).

Guo, et al., "Direct Fluorescence Analysis of Genetic Polymorphisms by Hybridization with Oligonucleotide Arrays on Glass Supports", *Nucleic Acids Research,* 22:5456–5465 (1994).

Johnston, et al., "Chemistry of High Density Arrays: Factors Impacting Issues of Complexity", (Abstract) *Microbial & Comparative Genomics,* 1:235 (1996).

Kallioniemi et al., "Comparative Genomic Hybridization for Molecular Cytogenic Analysis of Solid Tumors," *Science,* 258:818–821 (1992).

Kallioniemi et al., "Optimizing Comparative Genomic Hybridization for Analysis of DNA Sequence Copy Number Changes in Solid Tumors," *Genes, Chromosomes & Cancer,* 10:231–243 (1994).

Khrapko et al., "A Method for DNA Sequencing by Hybridization with Oligonucleotide Matrix," *DNA Sequencing and Mapping,* 1:375–388 (1991).

Kozal, et al., "Extensive Polymorphisms Observed in HIV–1 Clade B Protease Gene using High–Density Oligonucleotide Arrays", *Nature Medicine,* 2:753–759 (1996).

Kreiner, "Rapid Genetic Sequence Analysis Using a DNA Probe Array System," *American Laboratory* (Mar. 1996).

Lehrach et al., "Hybridization Fingerprinting in Genome Mapping and Sequencing," in *Genome Analysis,* vol. I: Genetic and Physical Mapping. (K.E. Davies & S.M. Tilgham, Eds.) Cold Spring Harbor Laboratory Press, pp. 39–81 (1990).

Lennon et al., "Hybridization Analyses of Arrayed cDNA Libraries," *Trends In Genetics,* 7:314–317 (1991).

Maskos, et al., "A Study of Oligonucleotide Reassociation Using Large Arrays of Oligonucleotides Synthesised on a Glass Support", *Nucleic Acids Research,* 21:4663–4669 (1993).

Medlin, "The Amazing Shrinking Laboratory", *Environmental Health Perspectives,* 103:244–246 (1995).

Nguyen et al., "Differential Gene Expression in the Murine Thymus Assayed by Quantitative Hybridization of Arrayed cDNA Clones," *Genomics,* 29:207–216 (1995).

Nowak, "Entering the Postgenome Era", *Science,* 270:368–369 (1995).

Pease, et al., "Light–generated Oligonucleotide Arrays for Rapid DNA Sequence Analysis", *Proc. Natl. Acad. Sci. USA,* 91:5022–5026 (May 1994).

Pietu, et al., "Novel Gene Transcripts Preferentially Expressed in Human Muscles Revealed by Quantitative Hybridization of a High Density cDNA Array", *Genome Research,* 6:492–503 (1996).

Regalado, "DNA—Chips in Genomics", *Start Up,* 1:24–30 (1996).

Sambrook, et al., "Molecular Cloning, A Laboratory Manual," *Cold Spring Harbor Press,* pp. 7.39–7.52 (1989).

Schena, et al., "Structure of Homeobox–Leucine Zipper Genes Suggests a Model for the Evolution of Gene Families", *Proc. Natl. Acad. Sci. USA,* 91:8393–8397 (Aug. 1994).

Schena, "Genome Analysis with Gene Expression Microarrays", *BioEssays,* 18:427–431 (1996).

Schena, et al., "Quantitative Monitoring of Gene Expression Patterns with a Complementary DNA Microarray," *Science,* 270:467–470 (1995).

Schena, et al., "Parallel Human Genome Analysis: Microarray–based Expression Monitoring in 1000 Genes", *Proc. Natl. Acad. Sci. USA,* 270:467–470 (1995).

Schena, et al., "The HAT4 Gene of *Arabidopsis* Encodes a Developmental Regulator", *Genes & Development,* 7:367–379 (1993).

Schena, et al., "HD–Zip Proteins: Members of an *Arabidopsis* Homeodomain Protein Superfamily", *Proc. Natl. Acad. Sci. USA,* 89:3894–3898 (May 1992).

Schober, et al., "Accurate High–Speed Liquid Handling of Very Small Biological Samples", *Biotechniques*, 15(2):324–329 (1993).

Shalon, "DNA Micro Arrays: A New Tool for Genetic Analysis" (Dec. 1995) (Ph.D. Thesis, Stanford University).

Shalon, et al., "A DNA Microarray System for Analyzing Complex DNA Samples Using Two–Color Fluorescent Probe Hybridization", *Genome Research*, 6:639–645 (Jul. 1996).

Southern, et al., "Analyzing and Compaing Nucleic Acid Sequences by Hybridization to Arrays of Oligonucleotides: Evaluation Using Experimental Models", *Genomics*, 13:1008–1017 (1992).

Woolley, et al., "Ultra–high–speed DNA Fragment Separations Using Microfabricated Capillary Array Electrophoresis Chips", *Proc. Natl. Acad. Sci. USA*, 91:11348–11352 (Nov. 1994).

Zhao et al., "High–Density cDNA Filter Analysis: A Novel Approach for Large–Scale, Quantitative Analysis of Gene Expression," *Science*, 156:207–213 (1995).

NIH grant application of P.O. Brown submitted 1992.

J.A., "Putting Genes on a Chip", *Science*, 264: (1994).

Eggers, M. et al., "A Microchip for Quantitative Detection of Molecules Utilizing Luminescent and Radioisotope Reporter Groups," *BioTechniques*, 17, pp. 516–525 (Sep. 1994).

De Risi, J. et al., "Use Of a cDNA Microarray to Analyse Gene Expression Patterns In Human Cancer," *Nature Genetics*, 14:457–460 (Dec. 1996).

METHODS FOR FABRICATING MICROARRAYS OF BIOLOGICAL SAMPLES

CROSS-REFERENCE TO RELATED APPLICATIONS

This application is a continuation of U.S. patent application Ser. No. 08/477,809, filed Jun. 7, 1995 and now U.S. Pat. No. 5,807,522, which is a continuation-in-part of U.S. patent application Ser. No. 08/261,388, filed Jun. 17, 1994 and now abandoned, both of which are incorporated herein by reference.

The United States government may have certain rights in the present invention pursuant to Grant No. HG00450 awarded by the National Institutes of Health.

FIELD OF THE INVENTION

This invention relates to a method and apparatus for fabricating microarrays of biological samples for large scale screening assays, such as arrays of DNA samples to be used in DNA hybridization assays for genetic research and diagnostic applications.

REFERENCES

Abouzied, et al., *Journal of AOAC International* 77(2) :495–500 (1994).

Bohlander, et al., *Genomics* 13:1322–1324 (1992).

Drmanac, et al., *Science* 260:1649–1652 (1993).

Fodor, et al., *Science* 251:767–773 (1991).

Khrapko, et al., *DNA Sequence* 1:375–388 (1991).

Kuriyama, et al. , *AN ISFET BIOSENSOR, APPLIED BIOSENSORS* (Donald Wise, Ed.), Butterworths, pp. 93–114 (1989).

Lehrach, et al., *HYBRIDIZATION FINGERPRINTING IN GENOME MAPPING AND SEQUENCING, GENOME ANALYSIS, VOL* 1 (Davies and Tilgham, Eds.), Cold Spring Harbor Press, pp. 39–81 (1990).

Maniatis, et al., *MOLECULAR CLONING, A LABORATORY MANUAL,* Cold Spring Harbor Press (1989).

Nelson, et al., *Nature Genetics* 4:11–18 (1993).

Pirrung, et al., U.S. Pat. No. 5,143,854 (1992).

Riles, et al. , *Genetics* 134:81–150 (1993).

Schena, M. et al., *Proc. Nat. Acad. Sci. USA* 89:3894–3898 (1992).

Southern, et al., *Genomics* 13:1008–1017 (1992).

BACKGROUND OF THE INVENTION

A variety of methods are currently available for making arrays of biological macromolecules, such as arrays of nucleic acid molecules or proteins. One method for making ordered arrays of DNA on a porous membrane is a "dot blot" approach. In this method, a vacuum manifold transfers a plurality, e.g., 96, aqueous samples of DNA from 3 millimeter diameter wells to a porous membrane. A common variant of this procedure is a "slot-blot" method in which the wells have highly-elongated oval shapes.

The DNA is immobilized on the porous membrane by baking the membrane or exposing it to UV radiation. This is a manual procedure practical for making one array at a time and usually limited to 96 samples per array. "Dot-blot" procedures are therefore inadequate for applications in which many thousand samples must be determined.

A more efficient technique employed for making ordered arrays of genomic fragments uses an array of pins dipped into the wells, e.g., the 96 wells of a microtitre plate, for transferring an array of samples to a substrate, such as a porous membrane. One array includes pins that are designed to spot a membrane in a staggered fashion, for creating an array of 9216 spots in a 22×22 cm area (Lehrach, et al., 1990). A limitation with this approach is that the volume of DNA spotted in each pixel of each array is highly variable. In addition, the number of arrays that can be made with each dipping is usually quite small.

An alternate method of creating ordered arrays of nucleic acid sequences is described by Pirrung, et al. (1992), and also by Fodor, et al. (1991). The method involves synthesizing different nucleic acid sequences at different discrete regions of a support. This method employs elaborate synthetic schemes, and is generally limited to relatively short nucleic acid sample, e.g., less than 20 bases. A related method has been described by Southern, et al. (1992).

Khrapko, et al. (1991) describes a method of making an oligonucleotide matrix by spotting DNA onto a thin layer of polyacrylamide. The spotting is done manually with a micropipette.

None of the methods or devices described in the prior art are designed for mass fabrication of microarrays characterized by (i) a large number of micro-sized assay regions separated by a distance of 50–200 microns or less, and (ii) a well-defined amount, typically in the picomole range, of analyte associated with each region of the array.

Furthermore, current technology is directed at performing such assays one at a time to a single array of DNA molecules. For example, the most common method for performing DNA hybridizations to arrays spotted onto porous membrane involves sealing the membrane in a plastic bag (Maniatas, et al., 1989) or a rotating glass cylinder (Robbins Scientific) with the labeled hybridization probe inside the sealed chamber. For arrays made on non-porous surfaces, such as a microscope slide, each array is incubated with the labeled hybridization probe sealed under a coverslip. These techniques require a separate sealed chamber for each array which makes the screening and handling of many such arrays inconvenient and time intensive.

Abouzied, et al. (1994) describes a method of printing horizontal lines of antibodies on a nitrocellulose membrane and separating regions of the membrane with vertical stripes of a hydrophobic material. Each vertical stripe is then reacted with a different antigen and the reaction between the immobilized antibody and an antigen is detected using a standard ELISA colorimetric technique. Abouzied's technique makes it possible to screen many one-dimensional arrays simultaneously on a single sheet of nitrocellulose. Abouzied makes the nitrocellulose somewhat hydrophobic using a line drawn with PAP Pen (Research Products International). However, Abouzied does not describe a technology that is capable of completely sealing the pores of the nitrocellulose. The pores of the nitrocellulose are still physically open and so the assay reagents can leak through the hydrophobic barrier during extended high temperature incubations or in the presence of detergents, which makes the Abouzied technique unacceptable for DNA hybridization assays.

Porous membranes with printed patterns of hydrophilic/hydrophobic regions exist for applications such as ordered arrays of bacteria colonies. QA Life Sciences (San Diego Calif.) makes such a membrane with a grid pattern printed on it. However, this membrane has the same disadvantage as the Abouzied technique since reagents can still flow between the gridded arrays making them unusable for separate DNA hybridization assays.

Pall Corporation make a 96-well plate with a porous filter heat sealed to the bottom of the plate. These plates are capable of containing different reagents in each well without cross-contamination. However, each well is intended to hold only one target element whereas the invention described here makes a microarray of many biomolecules in each subdivided region of the solid support. Furthermore, the 96 well plates are at least 1 cm thick and prevent the use of the device for many colorimetric, fluorescent and radioactive detection formats which require that the membrane lie flat against the detection surface. The invention described here requires no further processing after the assay step since the barriers elements are shallow and do not interfere with the detection step, thereby greatly increasing convenience.

Hyseq Corporation has described a method of making an "array of arrays" on a non-porous solid support for use with their sequencing by hybridization technique. The method described by Hyseq involves modifying the chemistry of the solid support material to form a hydrophobic grid pattern where each subdivided region contains a microarray of biomolecules. Hyseq's flat hydrophobic pattern does not make use of physical blocking as an additional means of preventing cross contamination.

SUMMARY OF THE INVENTION

The invention includes, in one aspect, a method of forming a microarray of analyte-assay regions on a solid support, where each region in the array has a known amount of a selected, analyte-specific reagent. The method involves first loading a solution of a selected analyte-specific reagent in a reagent-dispensing device having an elongate capillary channel (i) formed by spaced-apart, coextensive elongate members, (ii) adapted to hold a quantity of the reagent solution and (iii) having a tip region at which aqueous solution in the channel forms a meniscus. The channel is preferably formed by a pair of spaced-apart tapered elements.

The tip of the dispensing device is tapped against a solid support at a defined position on the support surface with an impulse effective to break the meniscus in the capillary channel, and deposit a selected volume of solution on the surface, preferably a selected volume in the range 0.01 to 100 nl. The two steps are repeated until the desired array is formed.

The method may be practiced in forming a plurality of such arrays, where the solution-depositing step is applied to a selected position on each of a plurality of solid supports at each repeat cycle.

The dispensing device may be loaded with a new solution, by the steps of (i) dipping the capillary channel of the device in a wash solution, (ii) removing wash solution drawn into the capillary channel, and (iii) dipping the capillary channel into the new reagent solution.

Also included in the invention is an automated apparatus for forming a microarray of analyte-assay regions on a plurality of solid supports, where each region in the array has a known amount of a selected, analyte-specific reagent. The apparatus has a holder for holding, at known positions, a plurality of planar supports, and a reagent dispensing device of the type described above.

The apparatus further includes a positioning structure for positioning the dispensing device at a selected array position with respect to a support in said holder, and a dispensing structure for moving the dispensing device into tapping engagement against a support with a selected impulse effective to deposit a selected volume on the support, e.g., a selected volume in the volume range 0.01 to 100 nl.

The positioning and dispensing structures are controlled by a control unit in the apparatus. The unit operates to (i) place the dispensing device at a loading station, (ii) move the capillary channel in the device into a selected reagent at the loading station, to load the dispensing device with the reagent, and (iii) dispense the reagent at a defined array position on each of the supports on said holder. The unit may further operate, at the end of a dispensing cycle, to wash the dispensing device by (i) placing the dispensing device at a washing station, (ii) moving the capillary channel in the device into a wash fluid, to load the dispensing device with the fluid, and (iii) removing the wash fluid prior to loading the dispensing device with a fresh selected reagent.

The dispensing device in the apparatus may be one of a plurality of such devices which are carried on the arm for dispensing different analyte assay reagents at selected spaced array positions.

In another aspect, the invention includes a substrate with a surface having a microarray of at least $10^3$ distinct polynucleotide or polypeptide biopolymers in a surface area of less than about 1 $cm^2$. Each distinct biopolymer (i) is disposed at a separate, defined position in said array, (ii) has a length of at least 50 subunits, and (iii) is present in a defined amount between about 0.1 femtomoles and 100 nanomoles.

In one embodiment, the surface is glass slide surface coated with a polycationic polymer, such as polylysine, and the biopolymers are polynucleotides. In another embodiment, the substrate has a water-impermeable backing, a water-permeable film formed on the backing, and a grid formed on the film. The grid is composed of intersecting water-impervious grid elements extending from said backing to positions raised above the surface of said film, and partitions the film into a plurality of water-impervious cells. A biopolymer array is formed within each well.

More generally, there is provided a substrate for use in detecting binding of labeled polynucleotides to one or more of a plurality different-sequence, immobilized polynucleotides. The substrate includes, in one aspect, a glass support, a coating of a polycationic polymer, such as polylysine, on said surface of the support, and an array of distinct polynucleotides electrostatically bound non-covalently to said coating, where each distinct biopolymer is disposed at a separate, defined position in a surface array of polynucleotides.

In another aspect, the substrate includes a water-impermeable backing, a water-permeable film formed on the backing, and a grid formed on the film, where the grid is composed of intersecting water-impervious grid elements extending from the backing to positions raised above the surface of the film, forming a plurality of cells. A biopolymer array is formed within each cell.

Also forming part of the invention is a method of detecting differential expression of each of a plurality of genes in a first cell type, with respect to expression of the same genes in a second cell type. In practicing the method, there is first produced fluorescent-labeled cDNAs from mRNAs isolated from the two cells types, where the cDNAs from the first and second cell types are labeled with first and second different fluorescent reporters.

A mixture of the labeled cDNAs from the two cell types is added to an array of polynucleotides representing a plurality of known genes derived from the two cell types, under conditions that result in hybridization of the cDNAs to complementary-sequence polynucleotides in the array. The array is then examined by fluorescence under fluorescence excitation conditions in which (i) polynucleotides in the array that are hybridized predominantly to cDNAs derived from one of the first or second cell types give a distinct first or second fluorescence emission color, respectively, and (ii) polynucleotides in the array that are hybridized to substantially equal numbers of cDNAs derived from the first and second cell types give a distinct combined fluorescence emission color, respectively. The relative expression of known genes in the two cell types can then be determined by the observed fluorescence emission color of each spot.

These and other objects and features of the invention will become more fully apparent when the following detailed description of the invention is read in conjunction with the accompanying figures.

The file of this patent contains at least one drawing executed in color. Copies of this patent with color drawing (s) will be provided by the Patent and Trademark Office upon request and payment of the necessary fee.

DETAILED DESCRIPTION OF THE INVENTION

I. Definitions

Figure 1:
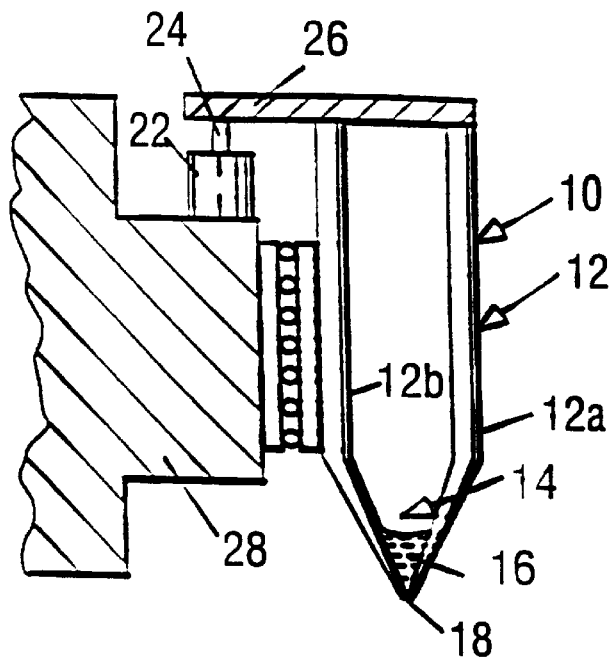
FIG. 1 is a side view of a reagent-dispensing device having a open-capillary dispensing head constructed for use in one embodiment of the invention.

Unless indicated otherwise, the terms defined below have the following meanings:

"Ligand" refers to one member of a ligand/anti-ligand binding pair. The ligand may be, for example, one of the nucleic acid strands in a complementary, hybridized nucleic acid duplex binding pair; an effector molecule in an effector/receptor binding pair; or an antigen in an antigen/antibody or antigen/antibody fragment binding pair.

"Anti-ligand" refers to the opposite member of a ligand/anti-ligand binding pair. The anti-ligand may be the other of the nucleic acid strands in a complementary, hybridized nucleic acid duplex binding pair; the receptor molecule in an effector/receptor binding pair; or an antibody or antibody fragment molecule in antigen/antibody or antigen/antibody fragment binding pair, respectively.

"Analyte" or "analyte molecule" refers to a molecule, typically a macromolecule, such as a polynucleotide or polypeptide, whose presence, amount, and/or identity are to be determined. The analyte is one member of a ligand/anti-ligand pair.

"Analyte-specific assay reagent" refers to a molecule effective to bind specifically to an analyte molecule. The reagent is the opposite member of a ligand/anti-ligand binding pair.

An "array of regions on a solid support" is a linear or two-dimensional array of preferably discrete regions, each having a finite area, formed on the surface of a solid support.

A "microarray" is an array of regions having a density of discrete regions of at least about 100/cm$^2$, and preferably at least about 1000/cm$^2$. The regions in a microarray have typical dimensions, e.g., diameters, in the range of between about 10–250 $\mu$m, and are separated from other regions in the array by about the same distance.

A support surface is "hydrophobic" if a aqueous-medium droplet applied to the surface does not spread out substantially beyond the area size of the applied droplet. That is, the surface acts to prevent spreading of the droplet applied to the surface by hydrophobic interaction with the droplet.

A "meniscus" means a concave or convex surface that forms on the bottom of a liquid in a channel as a result of the surface tension of the liquid.

"Distinct biopolymers", as applied to the biopolymers forming a microarray, means an array member which is distinct from other array members on the basis of a different biopolymer sequence, and/or different concentrations of the same or distinct biopolymers, and/or different mixtures of distinct or different-concentration biopolymers. Thus an array of "distinct polynucleotides" means an array containing, as its members, (i) distinct polynucleotides, which may have a defined amount in each member, (ii) different, graded concentrations of given-sequence polynucleotides, and/or (iii) different-composition mixtures of two or more distinct polynucleotides.

"Cell type" means a cell from a given source, e.g., a tissue, or organ, or a cell in a given state of differentiation, or a cell associated with a given pathology or genetic makeup.

II. Method of Microarray Formation

This section describes a method of forming a microarray of analyte-assay regions on a solid support or substrate, where each region in the array has a known amount of a selected, analyte-specific reagent.

FIG. 1 illustrates, in a partially schematic view, a reagent-dispensing device 10 useful in practicing the method. The device generally includes a reagent dispenser 12 having an elongate open capillary channel 14 adapted to hold a quantity of the reagent solution, such as indicated at 16, as will be described below. The capillary channel is formed by a pair of spaced-apart, coextensive, elongate members 12a, 12b which are tapered toward one another and converge at a tip or tip region 18 at the lower end of the channel. More generally, the open channel is formed by at least two elongate, spaced-apart members adapted to hold a quantity of reagent solutions and having a tip region at which aqueous solution in the channel forms a meniscus, such as the concave meniscus illustrated at 20 in FIG. 2A. The advantages of the open channel construction of the dispenser are discussed below.

With continued reference to FIG. 1, the dispenser device also includes structure for moving the dispenser rapidly toward and away from a support surface, for effecting deposition of a known amount of solution in the dispenser on a support, as will be described below with reference to FIGS. 2A–2C. In the embodiment shown, this structure includes a solenoid 22 which is activatable to draw a solenoid piston 24 rapidly downwardly, then release the piston, e.g., under spring bias, to a normal, raised position, as shown. The dispenser is carried on the piston by a connecting member 26, as shown. The just-described moving structure is also referred to herein as dispensing means for moving the dispenser into engagement with a solid support, for dispensing a known volume of fluid on the support.

The dispensing device just described is carried on an arm 28 that may be moved either linearly or in an x-y plane to position the dispenser at a selected deposition position, as will be described.

Figure 2A:
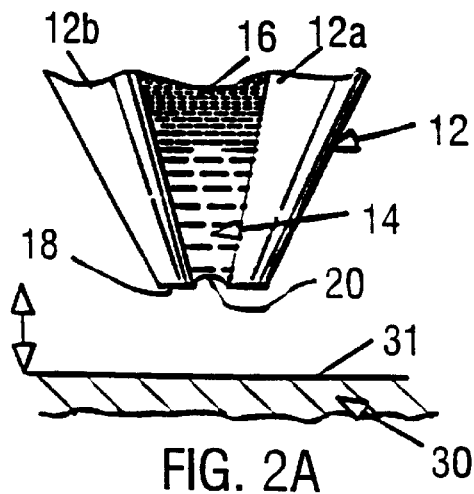
FIGS. 2A–2C illustrate steps in the delivery of a fixed-volume bead on a hydrophobic surface employing the dispensing head from FIG. 1, in accordance with one embodiment of the method of the invention.
Figure 2B:
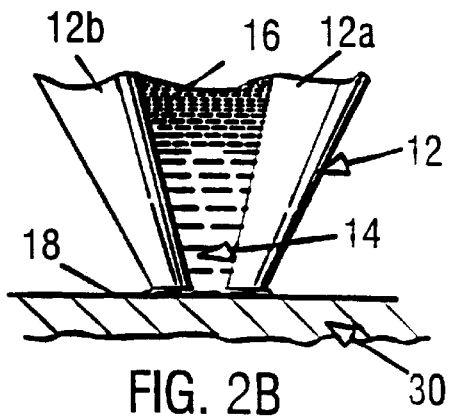
Figure 2C:
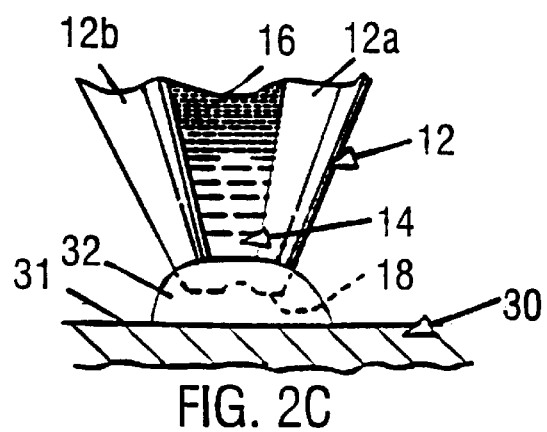

FIGS. 2A–2C illustrate the method of depositing a known amount of reagent solution in the just-described dispenser on the surface of a solid support, such as the support indicated at 30. The support is a polymer, glass, or other solid-material support having a surface indicated at 31.

In one general embodiment, the surface is a relatively hydrophilic, i.e., wettable surface, such as a surface having native, bound or covalently attached charged groups. One such surface described below is a glass surface having an absorbed layer of a polycationic polymer, such as poly-l-lysine.

In another embodiment, the surface has or is formed to have a relatively hydrophobic character, i.e., one that causes aqueous medium deposited on the surface to bead. A variety of known hydrophobic polymers, such as polystyrene, polypropylene, or polyethylene have desired hydrophobic properties, as do glass and a variety of lubricant or other hydrophobic films that may be applied to the support surface.

Initially, the dispenser is loaded with a selected analyte-specific reagent solution, such as by dipping the dispenser tip, after washing, into a solution of the reagent, and allowing filling by capillary flow into the dispenser channel. The dispenser is now moved to a selected position with respect to a support surface, placing the dispenser tip directly above the support-surface position at which the reagent is to be deposited. This movement takes place with the dispenser tip in its raised position, as seen in FIG. 2A, where the tip is typically at least several 1–5 mm above the surface of the substrate.

With the dispenser so positioned, solenoid 22 is now activated to cause the dispenser tip to move rapidly toward and away from the substrate surface, making momentary contact with the surface, in effect, tapping the tip of the dispenser against the support surface. The tapping movement of the tip against the surface acts to break the liquid meniscus in the tip channel, bringing the liquid in the tip into contact with the support surface. This, in turn, produces a flowing of the liquid into the capillary space between the tip and the surface, acting to draw liquid out of the dispenser channel, as seen in FIG. 2B.

FIG. 2C shows flow of fluid from the tip onto the support surface, which in this case is a hydrophobic surface. The figure illustrates that liquid continues to flow from the dispenser onto the support surface until it forms a liquid bead 32. At a given bead size, i.e., volume, the tendency of liquid to flow onto the surface will be balanced by the hydrophobic surface interaction of the bead with the support surface, which acts to limit the total bead area on the surface, and by the surface tension of the droplet, which tends toward a given bead curvature. At this point, a given bead volume will have formed, and continued contact of the dispenser tip with the bead, as the dispenser tip is being withdrawn, will have little or no effect on bead volume.

For liquid-dispensing on a more hydrophilic surface, the liquid will have less of a tendency to bead, and the dispensed volume will be more sensitive to the total dwell time of the dispenser tip in the immediate vicinity of the support surface, e.g., the positions illustrated in FIGS. 2B and 2C.

The desired deposition volume, i.e., bead volume, formed by this method is preferably in the range 2 pl (picoliters) to 2 nl (nanoliters), although volumes as high as 100 nl or more may be dispensed. It will be appreciated that the selected dispensed volume will depend on (i) the "footprint" of the dispenser tip, i.e., the size of the area spanned by the tip, (ii) the hydrophobicity of the support surface, and (iii) the time of contact with and rate of withdrawal of the tip from the support surface. In addition, bead size may be reduced by increasing the viscosity of the medium, effectively reducing the flow time of liquid from the dispenser onto the support surface. The drop size may be further constrained by depositing the drop in a hydrophilic region surrounded by a hydrophobic grid pattern on the support surface.

In a typical embodiment, the dispenser tip is tapped rapidly against the support surface, with a total residence time in contact with the support of less than about 1 msec, and a rate of upward travel from the surface of about 10 cm/sec.

Assuming that the bead that forms on contact with the surface is a hemispherical bead, with a diameter approximately equal to the width of the dispenser tip, as shown in FIG. 2C, the volume of the bead formed in relation to dispenser tip width (d) is given in Table 1 below. As seen, the volume of the bead ranges between 2 pl to 2 nl as the width size is increased from about 20 to 200 $\mu$m.

TABLE 1

| d | Volume (nl) |
| --- | --- |
| 20 $\mu$m | $2 \times 10^{-3}$ |
| 50 $\mu$m | $3.1 \times 10^{-2}$ |
| 100 $\mu$m | $2.5 \times 10^{-1}$ |
| 200 $\mu$m | 2 |

At a given tip size, bead volume can be reduced in a controlled fashion by increasing surface hydrophobicity, reducing time of contact of the tip with the surface, increasing rate or movement of the tip away from the surface, and/or increasing the viscosity of the medium. Once these parameters are fixed, a selected deposition volume in the desired pl to nl range can be achieved in a repeatable fashion.

After depositing a bead at one selected location on a support, the tip is typically moved to a corresponding position on a second support, a droplet is deposited at that position, and this process is repeated until a liquid droplet of the reagent has been deposited at a selected position on each of a plurality of supports.

The tip is then washed to remove the reagent liquid, filled with another reagent liquid and this reagent is now deposited at each another array position on each of the supports. In one embodiment, the tip is washed and refilled by the steps of (i) dipping the capillary channel of the device in a wash solution, (ii) removing wash solution drawn into the capillary channel, and (iii) dipping the capillary channel into the new reagent solution.

From the foregoing, it will be appreciated that the tweezers-like, open-capillary dispenser tip provides the advantages that (i) the open channel of the tip facilitates rapid, efficient washing and drying before reloading the tip with a new reagent, (ii) passive capillary action can load the sample directly from a standard microwell plate while retaining sufficient sample in the open capillary reservoir for the printing of numerous arrays, (iii) open capillaries are less prone to clogging than closed capillaries, and (iv) open capillaries do not require a perfectly faced bottom surface for fluid delivery.

Figure 3:
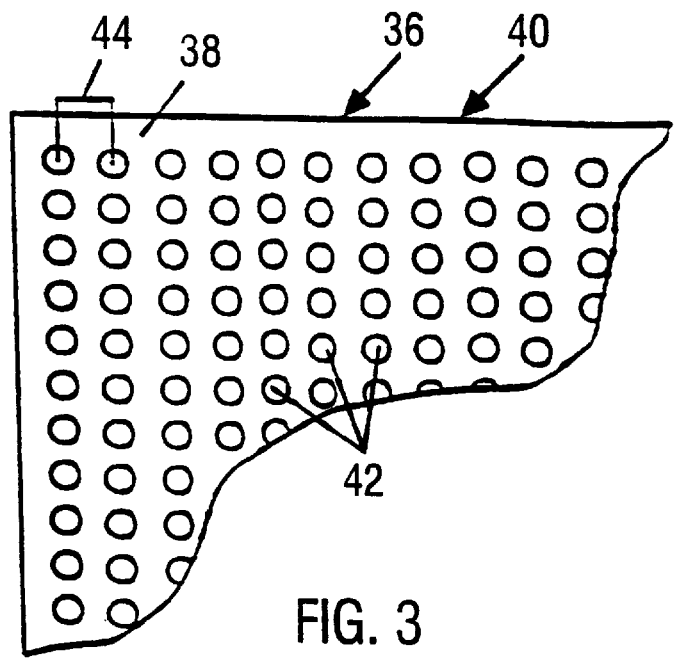
FIG. 3 shows a portion of a two-dimensional array of analyte-assay regions constructed according to the method of the invention.

A portion of a microarray 36 formed on the surface 38 of a solid support 40 in accordance with the method just described is shown in FIG. 3. The array is formed of a plurality of analyte-specific reagent regions, such as regions 42, where each region may include a different analyte-specific reagent. As indicated above, the diameter of each region is preferably between about 20–200 $\mu$m. The spacing between each region and its closest (non-diagonal) neighbor, measured from center-to-center (indicated at 44), is preferably in the range of about 20–400 $\mu$m. Thus, for example, an array having a center-to-center spacing of about 250 $\mu$m contains about 40 regions/cm or 1,600 regions/cm$^2$. After formation of the array, the support is treated to evaporate the liquid of the droplet forming each region, to leave a desired array of dried, relatively flat regions. This drying may be done by heating or under vacuum.

In some cases, it is desired to first rehydrate the droplets containing the analyte reagents to allow for more time for adsorption to the solid support. It is also possible to spot out the analyte reagents in a humid environment so that droplets do not dry until the arraying operation is complete.

III. Automated Apparatus for Forming Arrays

In another aspect, the invention includes an automated apparatus for forming an array of analyte-assay regions on a solid support, where each region in the array has a known amount of a selected, analyte-specific reagent.

Figure 4:
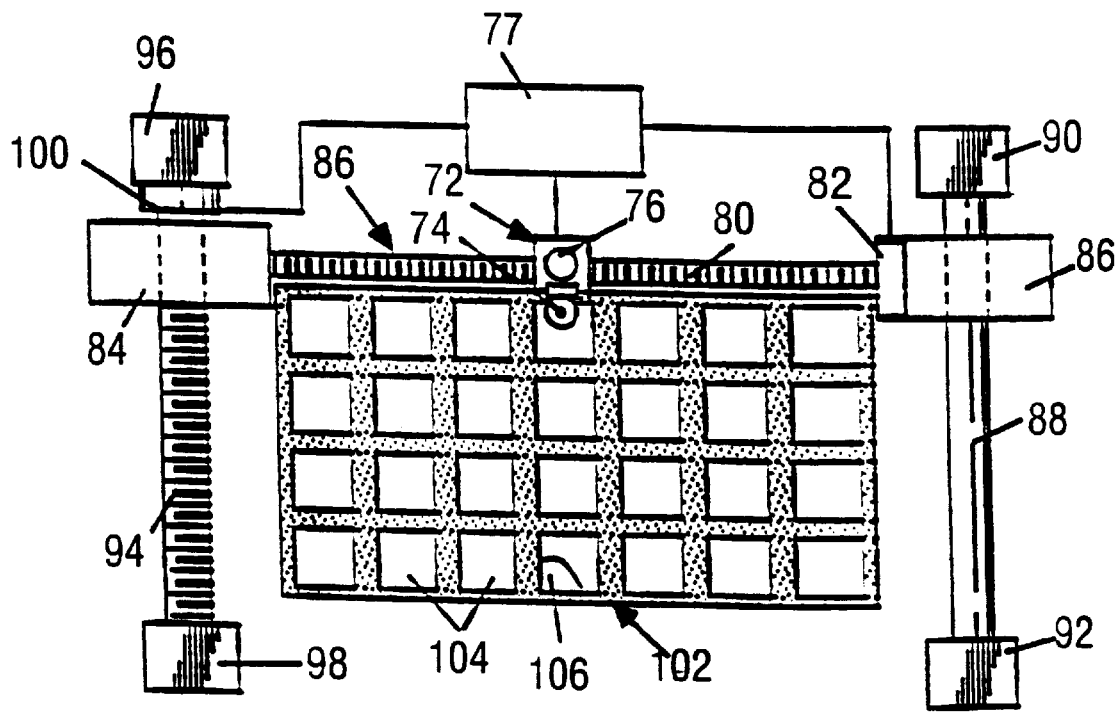
FIG. 4 is a planar view showing components of an automated apparatus for forming arrays in accordance with the invention.

The apparatus is shown in planar, and partially schematic view in FIG. 4. A dispenser device 72 in the apparatus has the basic construction described above with respect to FIG. 1, and includes a dispenser 74 having an open-capillary channel terminating at a tip, substantially as shown in FIGS. 1 and 2A–2C.

The dispenser is mounted in the device for movement toward and away from a dispensing position at which the tip of the dispenser taps a support surface, to dispense a selected volume of reagent solution, as described above. This movement is effected by a solenoid 76 as described above. Solenoid 76 is under the control of a control unit 77 whose operation will be described below. The solenoid is also referred to herein as dispensing means for moving the device into tapping engagement with a support, when the device is positioned at a defined array position with respect to that support.

The dispenser device is carried on an arm 74 which is threadedly mounted on a worm screw 80 driven (rotated) in a desired direction by a stepper motor 82 also under the control of unit 77. At its left end in the figure screw 80 is carried in a sleeve 84 for rotation about the screw axis. At its other end, the screw is mounted to the drive shaft of the stepper motor, which in turn is carried on a sleeve 86. The dispenser device, worm screw, the two sleeves mounting the worm screw, and the stepper motor used in moving the device in the "x" (horizontal) direction in the figure form what is referred to here collectively as a displacement assembly 86.

The displacement assembly is constructed to produce precise, micro-range movement in the direction of the screw, i.e., along an x axis in the figure. In one mode, the assembly functions to move the dispenser in x-axis increments having a selected distance in the range 5–25 $\mu$m. In another mode, the dispenser unit may be moved in precise x-axis increments of several microns or more, for positioning the dispenser at associated positions on adjacent supports, as will be described below.

The displacement assembly, in turn, is mounted for movement in the "y" (vertical) axis of the figure, for positioning the dispenser at a selected y axis position. The structure mounting the assembly includes a fixed rod 88 mounted rigidly between a pair of frame bars 90, 92, and a worm screw 94 mounted for rotation between a pair of frame bars 96, 98. The worm screw is driven (rotated) by a stepper motor 100 which operates under the control of unit 77. The motor is mounted on bar 96, as shown.

The structure just described, including worm screw 94 and motor 100, is constructed to produce precise, micro-range movement in the direction of the screw, I.e., along a y axis in the figure. As above, the structure functions in one mode to move the dispenser in y-axis increments having a selected distance in the range 5–250 $\mu$m, and in a second mode, to move the dispenser in precise y-axis increments of several microns ($\mu$m) or more, for positioning the dispenser at associated positions on adjacent supports.

The displacement assembly and structure for moving this assembly in the y axis are referred to herein collectively as positioning means for positioning the dispensing device at a selected array position with respect to a support.

A holder 102 in the apparatus functions to hold a plurality of supports, such as supports 104 on which the microarrays of reagent regions are to be formed by the apparatus. The holder provides a number of recessed slots, such as slot 106, which receive the supports, and position them at precise selected positions with respect to the frame bars on which the dispenser moving means is mounted.

As noted above, the control unit in the device functions to actuate the two stepper motors and dispenser solenoid in a sequence designed for automated operation of the apparatus in forming a selected microarray of reagent regions on each of a plurality of supports.

The control unit is constructed, according to conventional microprocessor control principles, to provide appropriate signals to each of the solenoid and each of the stepper motors, in a given timed sequence and for appropriate signalling time. The construction of the unit, and the settings that are selected by the user to achieve a desired array pattern, will be understood from the following description of a typical apparatus operation.

Initially, one or more supports are placed in one or more slots in the holder. The dispenser is then moved to a position directly above a well (not shown) containing a solution of the first reagent to be dispensed on the support(s). The dispenser solenoid is actuated now to lower the dispenser tip into this well, causing the capillary channel in the dispenser to fill. Motors 82, 100 are now actuated to position the dispenser at a selected array position at the first of the supports. Solenoid actuation of the dispenser is then effective to dispense a selected-volume droplet of that reagent at this location. As noted above, this operation is effective to dispense a selected volume preferably between 2 pl and 2 nl of the reagent solution.

The dispenser is now moved to the corresponding position at an adjacent support and a similar volume of the solution is dispensed at this position. The process is repeated until the reagent has been dispensed at this preselected corresponding position on each of the supports.

Where it is desired to dispense a single reagent at more than two array positions on a support, the dispenser may be moved to different array positions at each support, before moving the dispenser to a new support, or solution can be dispensed at individual positions on each support, at one selected position, then the cycle repeated for each new array position.

To dispense the next reagent, the dispenser is positioned over a wash solution (not shown), and the dispenser tip is dipped in and out of this solution until the reagent solution has been substantially washed from the tip. Solution can be removed from the tip, after each dipping, by vacuum, compressed air spray, sponge, or the like.

The dispenser tip is now dipped in a second reagent well, and the filled tip is moved to a second selected array position in the first support. The process of dispensing reagent at each of the corresponding second-array positions is then carried out as above. This process is repeated until an entire microarray of reagent solutions on each of the supports has been formed.

IV. Microarray Substrate

This section describes embodiments of a substrate having a microarray of biological polymers carried on the substrate surface. Subsection A describes a multi-cell substrate, each cell of which contains a microarray, and preferably an identical microarray, of distinct biopolymers, such as distinct polynucleotides, formed on a porous surface. Subsection B describes a microarray of distinct polynucleotides bound on a glass slide coated with a polycationic polymer.

A. Multi-Cell Substrate

Figure 9:
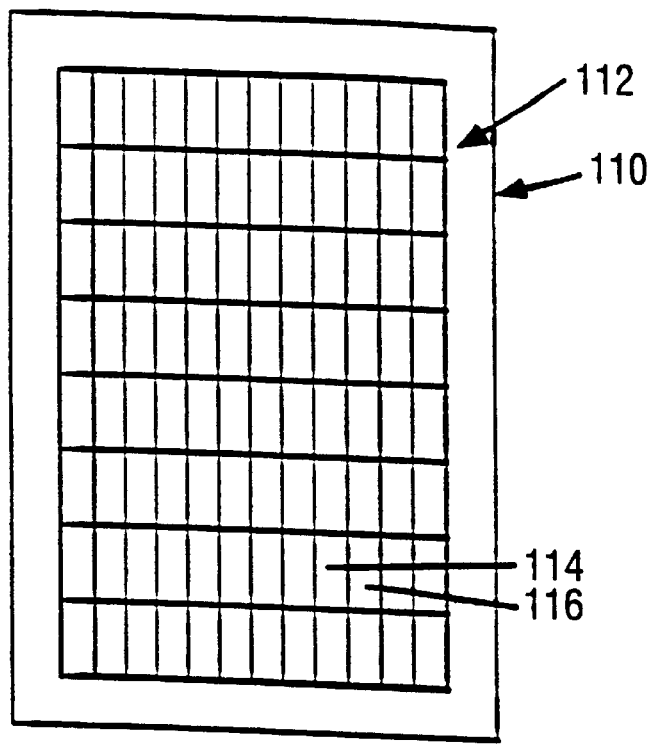
FIG. 9 shows a plan view of substrate having an array of cells formed by barrier elements in the form of a grid.
Figure 10:
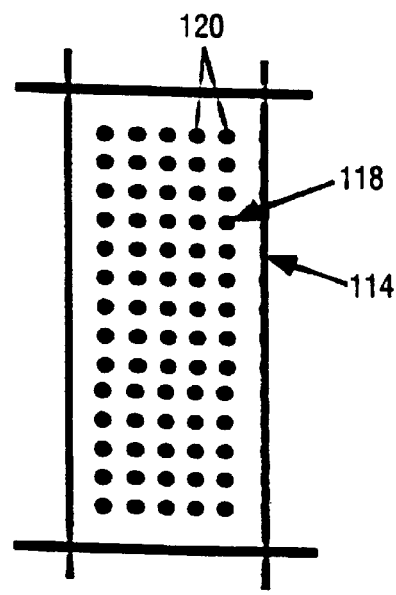
FIG. 10 shows an enlarged plan view of one of the cells in the substrate in FIG. 9, showing an array of polynucleotide regions in the cell.

FIG. 9 illustrates, in plan view, a substrate 110 constructed according to the invention. The substrate has an 8×12 rectangular array 112 of cells, such as cells 114, 116, formed on the substrate surface. With reference to FIG. 10, each cell, such as cell 114, in turn supports a microarray 118 of distinct biopolymers, such as polypeptides or polynucleotides at known, addressable regions of the microarray. Two such regions forming the microarray are indicated at 120, and correspond to regions, such as regions 42, forming the microarray of distinct biopolymers shown in FIG. 3.

The 96-cell array shown in FIG. 9 typically has array dimensions between about 12 and 244 mm in width and 8 and 400 mm in length, with the cells in the array having width and length dimension of $\frac{1}{12}$ and $\frac{1}{8}$ the array width and length dimensions, respectively, i.e., between about 1 and 20 in width and 1 and 50 mm in length.

Figure 11:
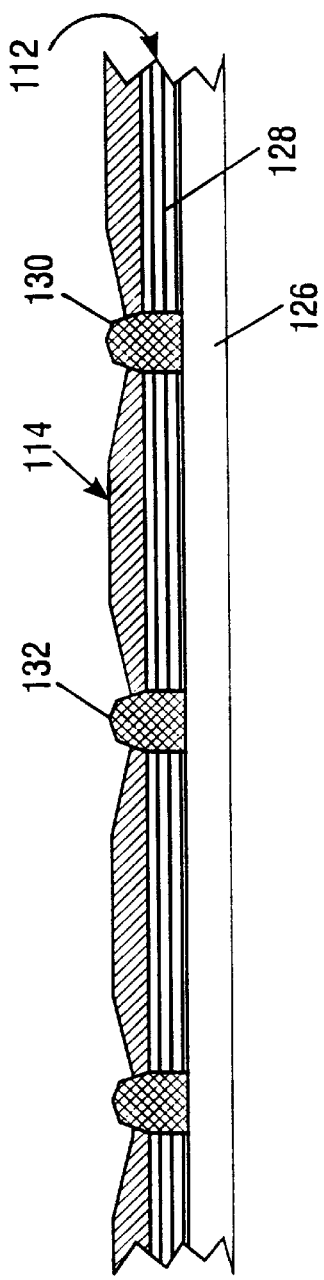
FIG. 11 is an enlarged sectional view of the substrate in FIG. 9, taken along a section line in that figure.

The construction of substrate is shown cross-sectionally in FIG. 11, which is an enlarged sectional view taken along view line 124 in FIG. 9. The substrate includes a water-impermeable backing 126, such as a glass slide or rigid polymer sheet. Formed on the surface of the backing is a water-permeable film 128. The film is formed of a porous membrane material, such as nitrocellulose membrane, or a porous web material, such as a nylon, polypropylene, or PVDF porous polymer material. The thickness of the film is preferably between about 10 and 1000 $\mu$m. The film may be applied to the backing by spraying or coating uncured material on the backing, or by applying a preformed membrane to the backing. The backing and film may be obtained as a preformed unit from commercial source, e.g., a plastic-backed nitrocellulose film available from Schleicher and Schuell Corporation.

With continued reference to FIG. 11, the film-covered surface in the substrate is partitioned into a desired array of cells by water-impermeable grid lines, such as lines 130, 132, which have infiltrated the film down to the level of the backing, and extend above the surface of the film as shown, typically a distance of 100 to 2000 $\mu$m above the film surface.

The grid lines are formed on the substrate by laying down an uncured or otherwise flowable resin or elastomer solution in an array grid, allowing the material to infiltrate the porous film down to the backing, then curing or otherwise hardening the grid lines to form the cell-array substrate.

One preferred material for the grid is a flowable silicone available from Loctite Corporation. The barrier material can be extruded through a narrow syringe (e.g., 22 gauge) using air pressure or mechanical pressure. The syringe is moved relative to the solid support to print the barrier elements as a grid pattern. The extruded bead of silicone wicks into the pores of the solid support and cures to form a shallow waterproof barrier separating the regions of the solid support.

In alternative embodiments, the barrier element can be a wax-based material or a thermoset material such as epoxy. The barrier material can also be a UV-curing polymer which is exposed to UV light after being printed onto the solid support. The barrier material may also be applied to the solid support using printing techniques such as silk-screen printing. The barrier material may also be a heat-seal stamping of the porous solid support which seals its pores and forms a water-impervious barrier element. The barrier material may also be a shallow grid which is laminated or otherwise adhered to the solid support.

In addition to plastic-backed nitrocellulose, the solid support can be virtually any porous membrane with or without a non-porous backing. Such membranes are readily available from numerous vendors and are made from nylon, PVDF, polysulfone and the like. In an alternative embodiment, the barrier element may also be used to adhere the porous membrane to a non-porous backing in addition to functioning as a barrier to prevent cross contamination of the assay reagents.

In an alternative embodiment, the solid support can be of a non-porous material. The barrier can be printed either before or after the microarray of biomolecules is printed on the solid support.

As can be appreciated, the cells formed by the grid lines and the underlying backing are water-impermeable, having side barriers projecting above the porous film in the cells. Thus, defined-volume samples can be placed in each well without risk of cross-contamination with sample material in adjacent cells. In FIG. 11, defined volumes samples, such as sample 134, are shown in the cells.

As noted above, each well contains a microarray of distinct biopolymers. In one general embodiment, the microarrays in the well are identical arrays of distinct biopolymers, e.g., different sequence polynucleotides. Such arrays can be formed in accordance with the methods described in Section II, by depositing a first selected polynucleotide at the same selected microarray position in each of the cells, then depositing a second polynucleotide at a different microarray position in each well, and so on until a complete, identical microarray is formed in each cell.

In a preferred embodiment, each microarray contains about $10^3$ distinct polynucleotide or polypeptide biopolymers per surface area of less than about 1 cm$^2$. Also in a preferred embodiment, the biopolymers in each microarray region are present in a defined amount between about 0.1 femtomoles and 100 nanomoles. The ability to form high-density arrays of biopolymers, where each region is formed of a well-defined amount of deposited material, can be achieved in accordance with the microarray-forming method described in Section II.

Also in a preferred embodiment, the biopolymers are polynucleotides having lengths of at least about 50 bp, i.e., substantially longer than oligonucleotides which can be formed in high-density arrays by schemes involving parallel, step-wise polymer synthesis on the array surface.

In the case of a polynucleotide array, in an assay procedure, a small volume of the labeled DNA probe mixture in a standard hybridization solution is loaded onto each cell. The solution will spread to cover the entire microarray and stop at the barrier elements. The solid support is then incubated in a humid chamber at the appropriate temperature as required by the assay.

Each assay may be conducted in an "open-face" format where no further sealing step is required, since the hybridization solution will be kept properly hydrated by the water vapor in the humid chamber. At the conclusion of the incubation step, the entire solid support containing the numerous microarrays is rinsed quickly enough to dilute the assay reagents so that no significant cross contamination occurs. The entire solid support is then reacted with detection reagents if needed and analyzed using standard colorimetric, radioactive or fluorescent detection means. All processing and detection steps are performed simultaneously to all of the microarrays on the solid support ensuring uniform assay conditions for all of the microarrays on the solid support.

B. Glass-Slide Polynucleotide Array

Figure 5:
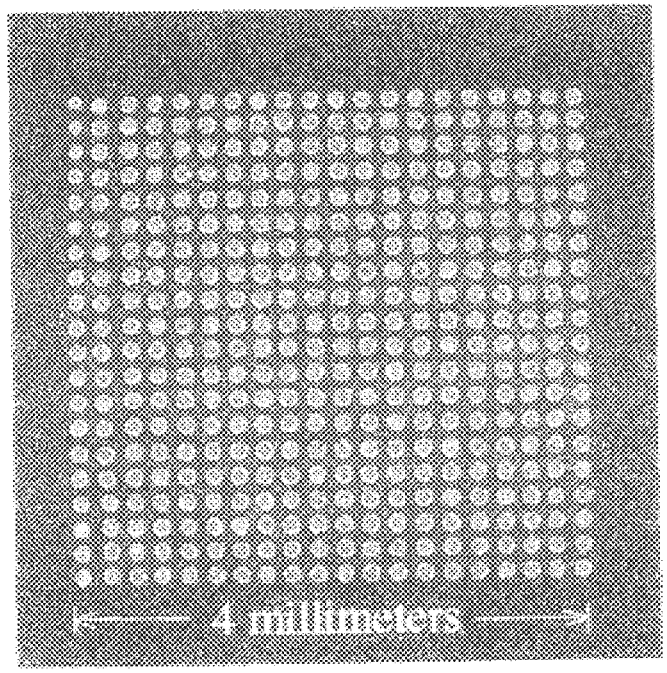
FIG. 5 shows a fluorescent image of an actual 20×20 array of 400 fluorescently-labeled DNA samples immobilized on a poly-l-lysine coated slide, where the total area covered by the 400 element array is 16 square millimeters.

FIG. 5 shows a substrate 136 formed according to another aspect of the invention, and intended for use in detecting binding of labeled polynucleotides to one or more of a plurality distinct polynucleotides. The substrate includes a glass substrate 138 having formed on its surface, a coating of a polycationic polymer, preferably a cationic polypeptide, such as polylysine or polyarginine. Formed on the polycationic coating is a microarray 140 of distinct polynucleotides, each localized at known selected array regions, such as regions 142.

The slide is coated by placing a uniform-thickness film of a polycationic polymer, e.g., poly-l-lysine, on the surface of a slide and drying the film to form a dried coating. The amount of polycationic polymer added is sufficient to form at least a monolayer of polymers on the glass surface. The polymer film is bound to surface via electrostatic binding between negative silyl-OH groups on the surface and charged amine groups in the polymers. Poly-l-lysine coated glass slides may be obtained commercially, e.g., from Sigma Chemical Co. (St. Louis, Mo.).

To form the microarray, defined volumes of distinct polynucleotides are deposited on the polymer-coated slide, as described in Section II. According to an important feature of the substrate, the deposited polynucleotides remain bound to the coated slide surface non-covalently when an aqueous DNA sample is applied to the substrate under conditions which allow hybridization of reporter-labeled polynucleotides in the sample to complementary-sequence (single-stranded) polynucleotides in the substrate array. The method is illustrated in Examples 1 and 2.

To illustrate this feature, a substrate of the type just described, but having an array of same-sequence polynucleotides, was mixed with fluorescent-labeled complementary DNA under hybridization conditions. After washing to remove non-hybridized material, the substrate was examined by low-power fluorescence microscopy. The array can be visualized by the relatively uniform labeling pattern of the array regions.

In a preferred embodiment, each microarray contains at least $10^3$ distinct polynucleotide or polypeptide biopolymers per surface area of less than about 1 cm$^2$. In the embodiment shown in FIG. 5, the microarray contains 400 regions in an area of about 16 mm$^2$, or 2.5×10$^3$ regions/cm$^2$. Also in a preferred embodiment, the polynucleotides in each microarray region are present in a defined amount between about 0.1 femtomoles and 100 nanomoles in the case of polynucleotides. As above, the ability to form high-density arrays of this type, where each region is formed of a well-defined amount of deposited material, can be achieved in accordance with the microarray-forming method described in Section II.

Also in a preferred embodiment, the polynucleotides have lengths of at least about 50 bp, i.e., substantially longer than oligonucleotides which can be formed in high-density arrays by various in situ synthesis schemes.

V. Utility

Microarrays of immobilized nucleic acid sequences prepared in accordance with the invention can be used for large scale hybridization assays in numerous genetic applications, including genetic and physical mapping of genomes, monitoring of gene expression, DNA sequencing, genetic diagnosis, genotyping of organisms, and distribution of DNA reagents to researchers.

For gene mapping, a gene or a cloned DNA fragment is hybridized to an ordered array of DNA fragments, and the identity of the DNA elements applied to the array is unambiguously established by the pixel or pattern of pixels of the array that are detected. One application of such arrays for creating a genetic map is described by Nelson, et al. (1993). In constructing physical maps of the genome, arrays of immobilized cloned DNA fragments are hybridized with other cloned DNA fragments to establish whether the cloned fragments in the probe mixture overlap and are therefore contiguous to the immobilized clones on the array. For example, Lehrach, et al., describe such a process.

The arrays of immobilized DNA fragments may also be used for genetic diagnostics. To illustrate, an array containing multiple forms of a mutated gene or genes can be probed with a labeled mixture of a patient's DNA which will preferentially interact with only one of the immobilized versions of the gene.

The detection of this interaction can lead to a medical diagnosis. Arrays of immobilized DNA fragments can also be used in DNA probe diagnostics. For example, the identity of a pathogenic microorganism can be established unambiguously by hybridizing a sample of the unknown pathogen's DNA to an array containing many types of known pathogenic DNA. A similar technique can also be used for unambiguous genotyping of any organism. Other molecules of genetic interest, such as cDNAs and RNAs can be immobilized on the array or alternately used as the labeled probe mixture that is applied to the array.

In one application, an array of cDNA clones representing genes is hybridized with total cDNA from an organism to monitor gene expression for research or diagnostic purposes. Labeling total cDNA from a normal cell with one color fluorophore and total cDNA from a diseased cell with another color fluorophore and simultaneously hybridizing the two cDNA samples to the same array of cDNA clones allows for differential gene expression to be measured as the ratio of the two fluorophore intensities. This two-color experiment can be used to monitor gene expression in different tissue types, disease states, response to drugs, or response to environmental factors. An example of this approach is illustrated in Example 2, described with respect to FIG. 8.

By way of example and without implying a limitation of scope, such a procedure could be used to simultaneously screen many patients against all known mutations in a disease gene. This invention could be used in the form of, for example, 96 identical 0.9 cm×2.2 cm microarrays fabricated on a single 12 cm×18 cm sheet of plastic-backed nitrocellulose where each microarray could contain, for example, 100 DNA fragments representing all known mutations of a given gene. The region of interest from each of the DNA samples from 96 patients could be amplified, labeled, and hybridized to the 96 individual arrays with each assay performed in 100 microliters of hybridization solution. The approximately 1 thick silicone rubber barrier elements between individual arrays prevent cross-contamination of the patient samples by sealing the pores of the nitrocellulose and by acting as a physical barrier between each microarray. The solid support containing all 96 microarrays assayed with the 96 patient samples is incubated, rinsed, detected and analyzed as a single sheet of material using standard radioactive, fluorescent, or colorimetric detection means (Maniatas, et al., 1989). Previously, such a procedure would involve the handling, processing and tracking of 96 separate membranes in 96 separate sealed chambers. By processing all 96 arrays as a single sheet of material, significant time and cost savings are possible.

The assay format can be reversed where the patient or organism's DNA is immobilized as the array elements and each array is hybridized with a different mutated allele or genetic marker. The gridded solid support can also be used for parallel non-DNA ELISA assays. Furthermore, the invention allows for the use of all standard detection methods without the need to remove the shallow barrier elements to carry out the detection step.

In addition to the genetic applications listed above, arrays of whole cells, peptides, enzymes, antibodies, antigens, receptors, ligands, phospholipids, polymers, drug cogener preparations or chemical substances can be fabricated by the means described in this invention for large scale screening assays in medical diagnostics, drug discovery, molecular biology, immunology and toxicology.

The multi-cell substrate aspect of the invention allows for the rapid and convenient screening of many DNA probes against many ordered arrays of DNA fragments. This eliminates the need to handle and detect many individual arrays for performing mass screenings for genetic research and diagnostic applications. Numerous microarrays can be fabricated on the same solid support and each microarray reacted with a different DNA probe while the solid support is processed as a single sheet of material.

The following examples illustrate, but in no way are intended to limit, the present invention.

EXAMPLE 1

Genomic-Complexity Hybridization to DNA Microarrays Representing the Yeast *Saccharomyces cerevisiae* Genome with Two-Color Fluorescent Detection The array elements were randomly amplified PCR (Bohlander, et al., 1992) products using physically mapped lambda clones of *S. cerevisiae* genomic DNA as templates (Riles, et al., 1993). The PCR was performed directly on the lambda phage lysates, resulting in an amplification of both the 35 kb lambda vector and the 5–15 kb yeast insert sequences in the form of a uniform distribution of PCR product between 250–1500 base pairs in length. The PCR product was purified using Sephadex G50 gel filtration (Pharmacia, Piscataway, N.J.) and concentrated by evaporation to dryness at room temperature overnight. Each of the 864 amplified lambda clones was rehydrated in 15 µl of 3×SSC in preparation for spotting onto the glass.

The microarrays were fabricated on microscope slides which were coated with a layer of poly-l-lysine (Sigma). The automated apparatus described in Section III loaded 1 µl of the concentrated lambda clone PCR product in 3×SSC directly from 96 well storage plates into the open capillary printing element and deposited ~5 nl of sample per slide at 380 micron spacing between spots, on each of 40 slides. The process was repeated for all 864 samples and 8 control spots. After the spotting operation was complete, the slides were rehydrated in a humid chamber for 2 hours, baked in a dry 80° vacuum oven for 2 hours, rinsed to remove unabsorbed DNA and then treated with succinic anhydride to reduce non-specific adsorption of the labeled hybridization probe to the poly-l-lysine coated glass surface. Immediately prior to use, the immobilized DNA on the array was denatured in distilled water at 90° for 2 minutes.

For the pooled chromosome experiment, the 16 chromosomes of *Saccharomyces cerevisiae* were separated in a CHEF agarose gel apparatus (Biorad, Richmond, Calif.). The six largest chromosomes were isolated in one gel slice and the ten smallest chromosomes in a second gel slice. The DNA was recovered using a gel extraction kit (Qiagen, Chatsworth, Calif.). The two chromosome pools were randomly amplified in a manner similar to that used for the target lambda clones. Following amplification, 5 micrograms of each of the amplified chromosome pools were separately random-primer labeled using Klenow polymerase (Amersham, Arlington Heights, Ill.) with a lissamine conjugated nucleotide analog (Dupont NEN, Boston, Mass.) for the pool containing the six largest chromosomes, and with a fluorescein conjugated nucleotide analog (BMB) for the pool containing ten smallest chromosomes. The two pools were mixed and concentrated using an ultrafiltration device (Amicon, Danvers, Mass.).

Five micrograms of the hybridization probe consisting of both chromosome pools in 7.5 µl of TE was denatured in a boiling water bath and then snap cooled on ice. 2.5 µl of concentrated hybridization solution (5×SSC and 0.1% SDS) was added and all 10 µl transferred to the array surface, covered with a cover slip, placed in a custom-built single-slide humidity chamber and incubated at 60° for 12 hours. The slides were then rinsed at room temperature in 0.1×SSC and 0.1% SDS for 5 minutes, cover-slipped and scanned.

A custom built laser fluorescent scanner was used to detect the two-color hybridization signals from the 1.8×1.8 cm array at 20 micron resolution. The scanned image was gridded and analyzed using custom image analysis software. After correcting for optical crosstalk between the fluorophores due to their overlapping emission spectra, the red and green hybridization values for each clone on the array were correlated to the known physical map position of the clone resulting in a computer-generated color karyotype of the yeast genome.

Figure 6:
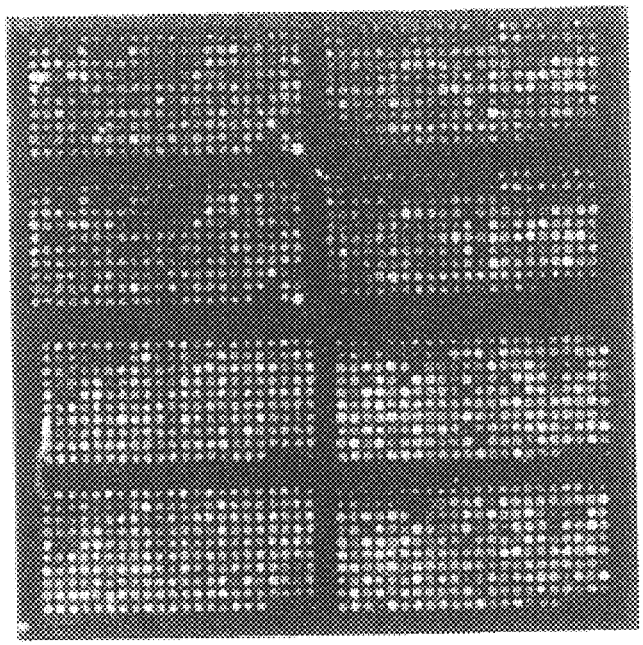
FIG. 6 is a fluorescent image of a 1.8 cm×1.8 cm microarray containing lambda clones with yeast inserts, the fluorescent signal arising from the hybridization to the array with approximately half the yeast genome labeled with a green fluorophore and the other half with a red fluorophore.

FIG. 6 shows the hybridization pattern of the two chromosome pools. A red signal indicates that the lambda clone on the array surface contains a cloned genomic DNA segment from one of the six largest yeast chromosomes. A green signal indicates that the lambda clone insert comes from one of the ten smallest yeast chromosomes. Orange signals indicate repetitive sequences which cross hybridized to both chromosome pools. Control spots on the array confirm that the hybridization is specific and reproducible.

Figure 7:
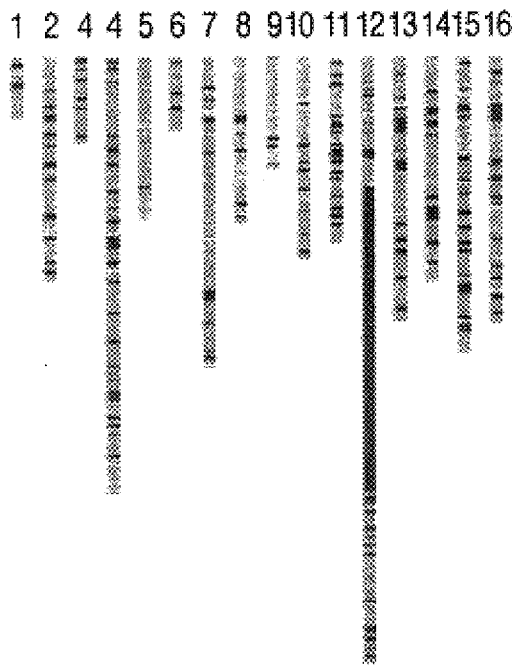
FIG. 7 shows the translation of the hybridization image of FIG. 6 into a karyotype of the yeast genome, where the elements of FIG.-6 microarray contain yeast DNA sequences that have been previously physically mapped in the yeast genome.

The physical map locations of the genomic DNA fragments contained in each of the clones used as array elements have been previously determined by Olson and co-workers (Riles, et al.), allowing for the automatic generation of the color karyotype shown in FIG. 7. The color of a chromosomal section on the karyotype corresponds to the color of the array element containing the clone from that section. The black regions of the karyotype represent false negative dark spots on the array (10%) or regions of the genome not covered by the Olson clone library (90%). Note that the six largest chromosomes are mainly red while the ten smallest chromosomes are mainly green, thus matching the original CHEF gel isolation of the hybridization probe. Areas of the red chromosomes containing green spots and vice-versa are probably due to spurious sample tracking errors in the formation of the original library and in the amplification and spotting procedures.

The yeast genome arrays have also been probed with individual clones or pools of clones that are fluorescently labeled for physical mapping purposes. The hybridization signals of these clones to the array were translated into positions on the physical map of the yeast genome.

EXAMPLE 2

Total cDNA Hybridized to Micro Arrays of cDNA Clones with Two-Color Fluorescent Detection Twenty-four clones containing cDNA inserts from the plant Arabidopsis were amplified using PCR. Salt was added to the purified PCR products to a final concentration of 3×SSC. The cDNA clones were spotted on poly-l-lysine coated microscope slides in a manner similar to Example 1. Among the cDNA clones was a clone representing a transcription factor, HAT4, which had previously been used to create a transgenic line of the plant Arabidopsis, in which this gene is present at ten times the level found in wild-type Arabidopsis (Schena, et al., 1992).

Figure 8:
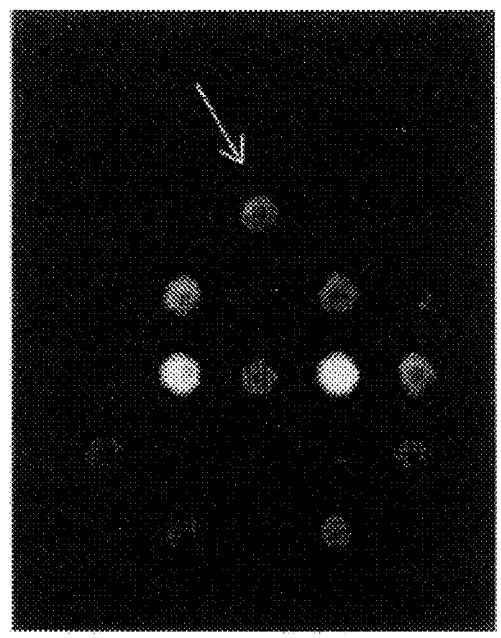
FIG. 8 shows a fluorescent image of a 0.5 cm×0.5 cm microarray of 24 cDNA clones, where the microarray was hybridized simultaneously with total cDNA from wild type Arabidopsis plant labeled with a green fluorophore and total cDNA from a transgenic Arabidopsis plant labeled with a red fluorophore, and the arrow points to the cDNA clone representing the gene introduced into the transgenic Arabidopsis plant.

Total poly-A mRNA from wild type Arabidopsis was isolated using standard methods (Maniatis, et al., 1989) and reverse transcribed into total cDNA, using a fluorescein nucleotide analog to label the cDNA product (green fluorescence). A similar procedure was performed with the transgenic line of Arabidopsis where the transcription factor HAT4 was inserted into the genome using standard gene transfer protocols. cDNA copies of mRNA from the transgenic plant are labeled with a lissamine nucleotide analog (red fluorescence). Two micrograms of the cDNA products from each type of plant were pooled together and hybridized to the cDNA clone array in a 10 microliter hybridization reaction in a manner similar to Example 1. Rinsing and detection of hybridization was also performed in a manner similar to Example 1. FIG. 8 shows the resulting hybridization pattern of the array.

Genes equally expressed in wild type and the transgenic Arabidopsis appeared yellow due to equal contributions of the green and red fluorescence to the final signal. The dots are different intensities of yellow indicating various levels of gene expression. The cDNA clone representing the transcription factor HAT4, expressed in the transgenic line of Arabidopsis but not detectably expressed in wild type Arabidopsis, appears as a red dot (with the arrow pointing to it), indicating the preferential expression of the transcription factor in the red-labeled transgenic Arabidopsis and the relative lack of expression of the transcription factor in the green-labeled wild type Arabidopsis.

An advantage of the microarray hybridization format for gene expression studies is the high partial concentration of each cDNA species achievable in the 10 microliter hybridization reaction. This high partial concentration allows for detection of rare transcripts without the need for PCR amplification of the hybridization probe which may bias the true genetic representation of each discrete cDNA species.

Gene expression studies such as these can be used for genomics research to discover which genes are expressed in which cell types, disease states, development states or environmental conditions. Gene expression studies can also be used for diagnosis of disease by empirically correlating gene expression patterns to disease states.

EXAMPLE 3

Multiplexed Colorimetric Hybridization on a Gridded Solid Support

Figure 12:
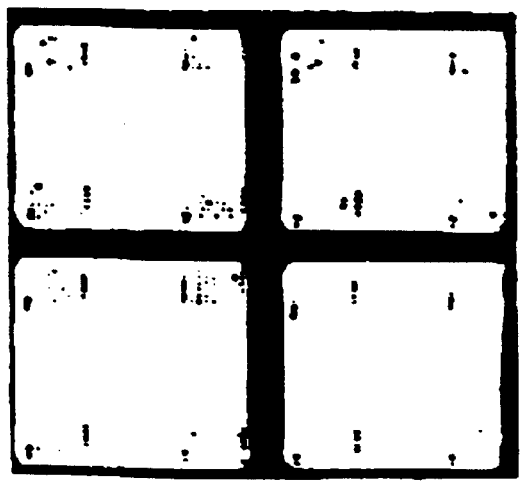
FIG. 12 is a scanned image of a 3 cm×3 cm nitrocellulose solid support containing four identical arrays of M13 clones in each of four quadrants, where each quadrant was hybridized simultaneously to a different oligonucleotide using an open face hybridization method.

A sheet of plastic-backed nitrocellulose was gridded with barrier elements made from silicone rubber according to the description in Section IV-A. The sheet was soaked in 10×SSC and allowed to dry. As shown in FIG. 12, 192 M13 clones, each with a different yeast inserts were arrayed 400 microns apart in four quadrants of the solid support using the automated device described in Section III. The bottom left quadrant served as a negative control for hybridization, while each of the other three quadrants was hybridized simultaneously with a different oligonucleotide using the open-face hybridization technology described in Section IV-A. The first two and last four elements of each array are positive controls for the colorimetric detection step.

The oligonucleotides were labeled with fluorescein, which was detected using an anti-fluorescein antibody conjugated to alkaline phosphatase that precipitated an NBT/BCIP dye on the solid support (Amersham). Perfect matches between the labeled oligos and the M13 clones resulted in dark spots visible to the naked eye and detected using an optical scanner (HP ScanJet II) attached to a personal computer. The hybridization patterns are different in every quadrant indicating that each oligo found several unique M13 clones from among the 192 with a perfect sequence match. Note that the open capillary printing tip leaves detectable dimples on the nitrocellulose which can be used to automatically align and analyze the images.

Although the invention has been described with respect to specific embodiments and methods, it will be clear that various changes and modification may be made without departing from the invention.

It is claimed:

1. A method of forming a microarray of discrete analyte-assay regions on a solid support, where each discrete region in the microarray has a select(d, analyte-specific reagent, said method comprising, (a) loading a solution of a selected analyte-specific reagent in a reagent-dispensing device having an elongate capillary channel adapted to hold a quantity of the reagent solution and having a tip region at which the channel is open-sided and the solution in the channel forms a meniscus, (b) tapping the tip of the dispensing device against a solid support at a defined position on the surface, with an impulse effective to break the meniscus in the capillary channel and deposit a selected volume of solution on the surface, and (c) repeating steps (a) and (b) until said microarray is formed.

2. The method of claim 1, wherein the reagents used to form the discrete regions in the microarray are distinct nucleic acid strands and wherein steps (a) and (b) are repeated until the microarray has about 100 or more discrete regions of distinct nucleic acid strands per $cm^2$ of solid support.

3. The method of claim 1, wherein the reagents used to form the discrete regions in the microarray are distinct nucleic acid strands and wherein steps (a) and (b) are repeated until the microarray has about 1000 or more discrete regions of distinct nucleic acid strands per $cm^2$ of solid support.

4. The method of claim 1, which further includes, after performing steps (a) and (b), reloading the reagent-dispensing device with a new reagent solution by the steps of (i) dipping the capillary channel of the device in a wash solution, (ii) removing wash solution drawn into the capillary channel, and (iii) dipping the capillary channel into the new reagent solution.

* * * * *

UNITED STATES PATENT AND TRADEMARK OFFICE
CERTIFICATE OF CORRECTION

| | |
|---|---|
| PATENT NO. | : 6,110,426 |
| APPLICATION NO. | : 09/001027 |
| DATED | : August 29, 2000 |
| INVENTOR(S) | : Tidhar Dari Shalon and Patrick O. Brown |

It is certified that error appears in the above-identified patent and that said Letters Patent is hereby corrected as shown below:

Column 1, lines 13-15, delete "The United States government may have certain rights in the present invention pursuant to Grant No. HG00450 by the National Institutes of Health." and insert --This invention was made with Government support under contract HL002668 awarded by the National Institutes of Health. The Government has certain rights in this invention.--

Signed and Sealed this

Twenty-fifth Day of May, 2010

David J. Kappos
*Director of the United States Patent and Trademark Office*